(12) United States Patent
Burnett et al.

(10) Patent No.: US 7,850,704 B2
(45) Date of Patent: Dec. 14, 2010

(54) METHOD AND APPARATUS FOR ANCHORING IMPLANTS

(75) Inventors: Daniel Rogers Burnett, San Francisco, CA (US); Shane Mangrum, Ammon, ID (US)

(73) Assignee: TheraNova, LLC, San Francisco, CA (US)

( * ) Notice: Subject to any disclaimer, the term of this patent is extended or adjusted under 35 U.S.C. 154(b) by 189 days.

(21) Appl. No.: 11/234,802

(22) Filed: Sep. 26, 2005

(65) Prior Publication Data
US 2006/0069400 A1 Mar. 30, 2006

Related U.S. Application Data

(60) Provisional application No. 60/613,205, filed on Sep. 27, 2004.

(51) Int. Cl.
*A61B 17/08* (2006.01)
(52) U.S. Cl. .................................................. 606/153
(58) Field of Classification Search .............. 623/2.1, 623/20.17, 20.2, 22.23, 1.13–1.36, 2.14–2.19, 623/2.4, 2.41
See application file for complete search history.

(56) References Cited

U.S. PATENT DOCUMENTS

| | | | | |
|---|---|---|---|---|
| 5,411,552 A | * | 5/1995 | Andersen et al. | 623/2.18 |
| 5,725,593 A | * | 3/1998 | Caracciolo | 623/22.23 |
| 6,053,940 A | * | 4/2000 | Wijay | 623/1.15 |
| 6,080,163 A | * | 6/2000 | Hussein et al. | 606/108 |
| 6,334,873 B1 | * | 1/2002 | Lane et al. | 623/2.14 |
| 7,175,652 B2 | * | 2/2007 | Cook et al. | 623/1.13 |
| 2002/0128719 A1 | * | 9/2002 | Burkinshaw | 623/20.2 |

* cited by examiner

*Primary Examiner*—Kevin T Truong
(74) *Attorney, Agent, or Firm*—Levine Bagade Han LLP

(57) ABSTRACT

Methods, devices and systems facilitate retention of a variety of therapeutic devices. Devices generally include an anchoring element, which has been designed to promote fibrotic ingrowth, and an anchored device, which has been designed to firmly engage the complementary region of the anchoring element. The anchoring element may be placed in a minimally invasive procedure temporally separated from the deployment of the anchored device. Once enough time has passed to ensure appropriate fixation of the anchoring element by tissue and cellular ingrowth at the site of placement, the anchored device may then be deployed during which it firmly engages the complementary region of the anchoring element. In this manner, a firm attachment to the implantation site may be made with a minimum of required hardware. Some embodiments are delivered through a delivery tube or catheter and while some embodiments may require laparoscopy or open surgery for one or more of the placement procedures. Some embodiments anchor devices within the cardiovascular tree while others may anchor devices within the gastrointestinal, peritoneal, pleural, pulmonary, urogynecologic, nasopharyngeal or dermatologic regions of the body.

22 Claims, 12 Drawing Sheets

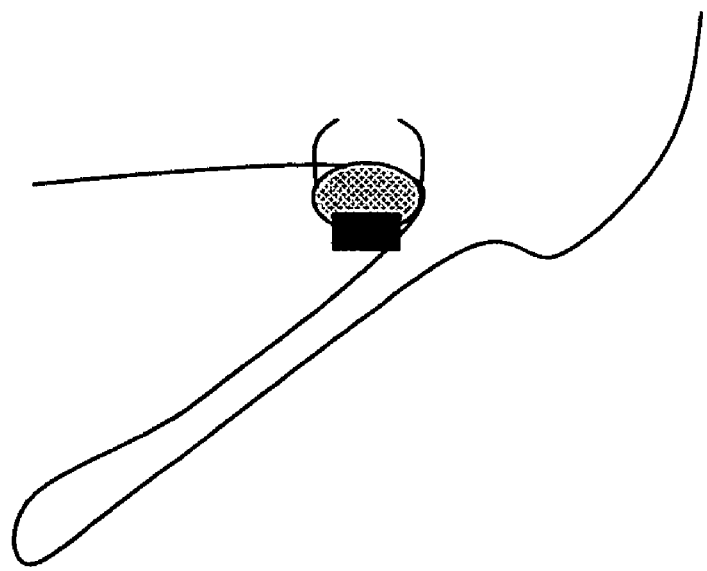
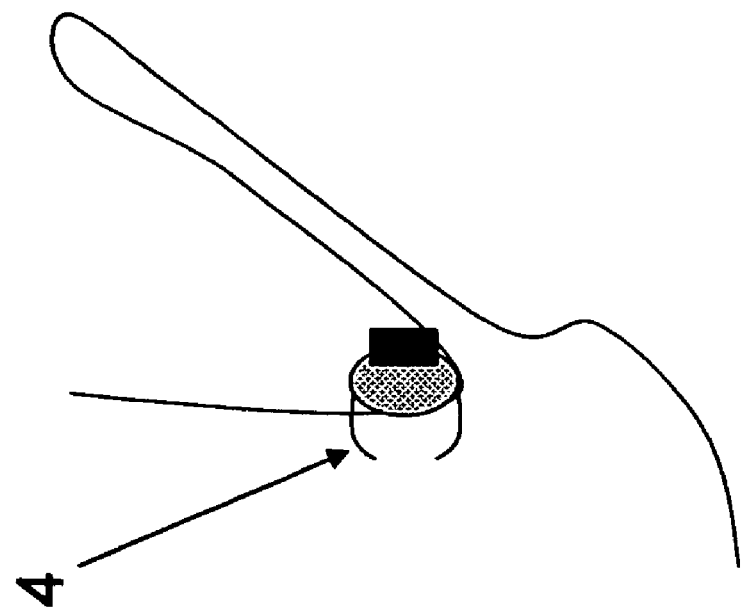
Figure 2

Figure 3
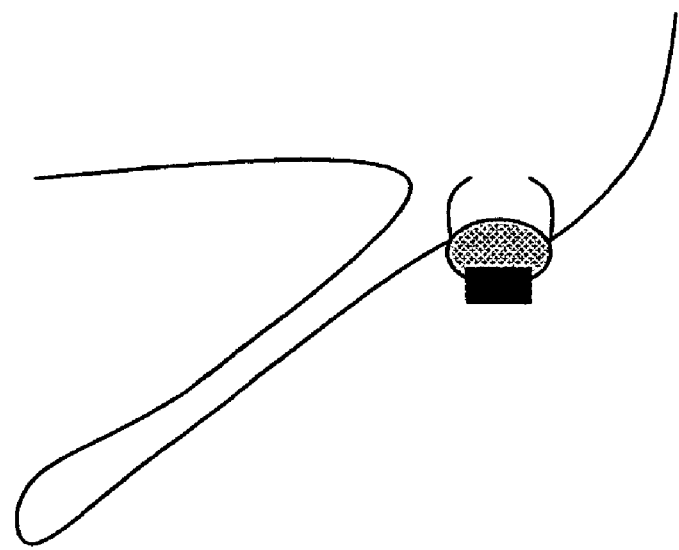
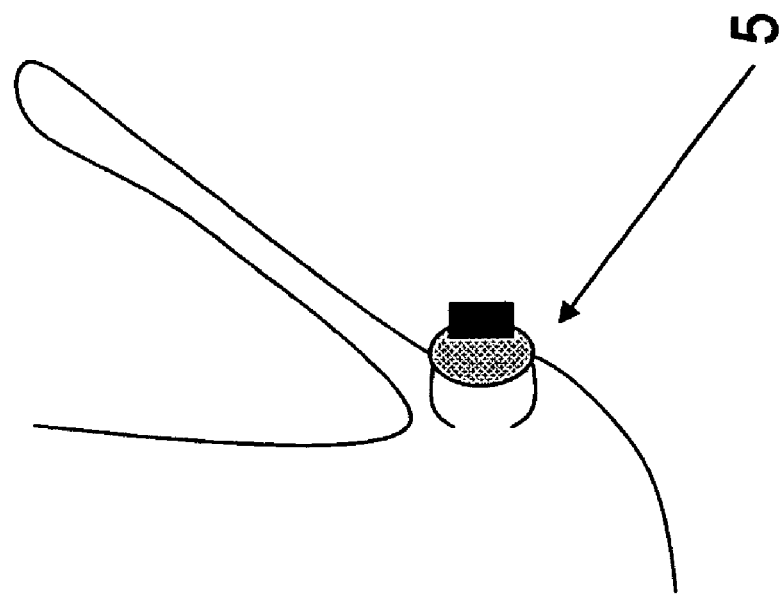

Figures 5A-B

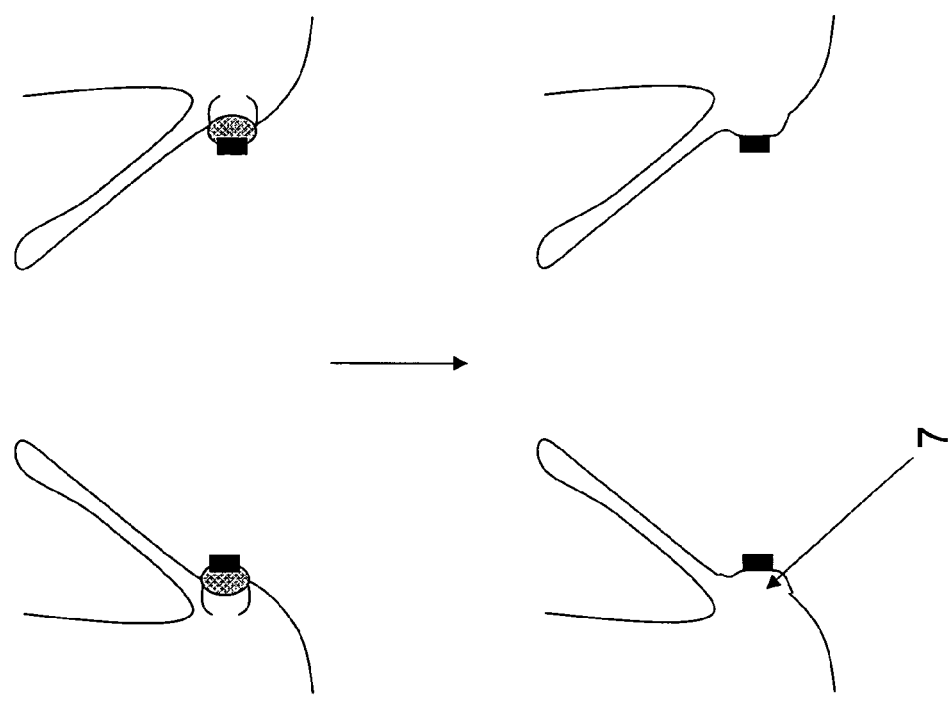

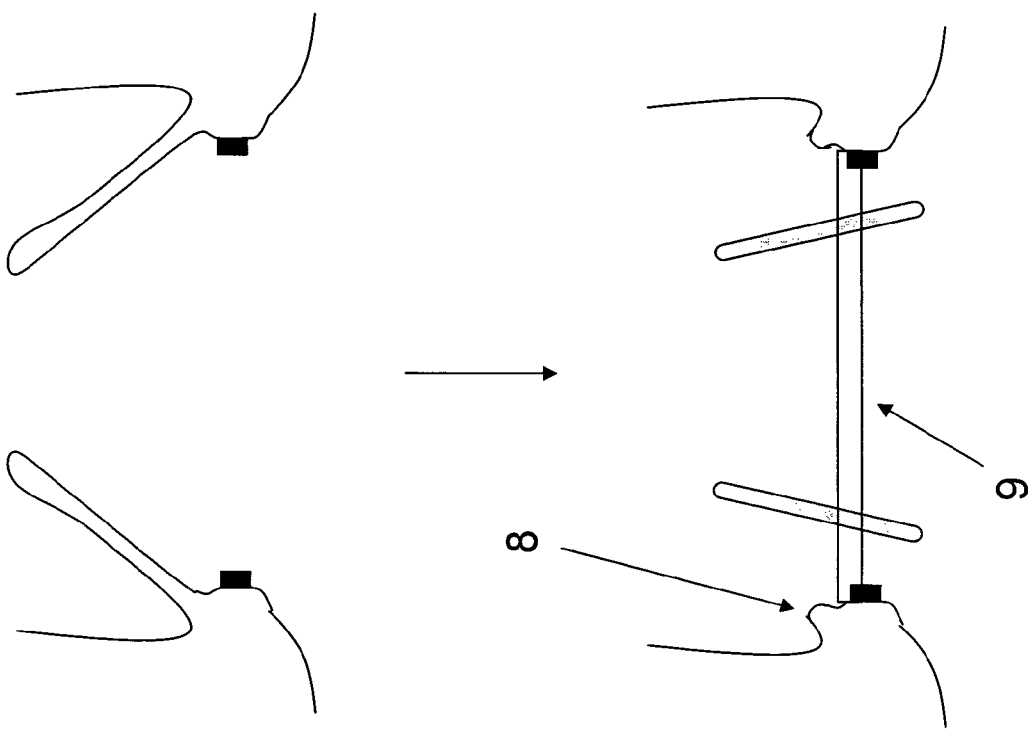

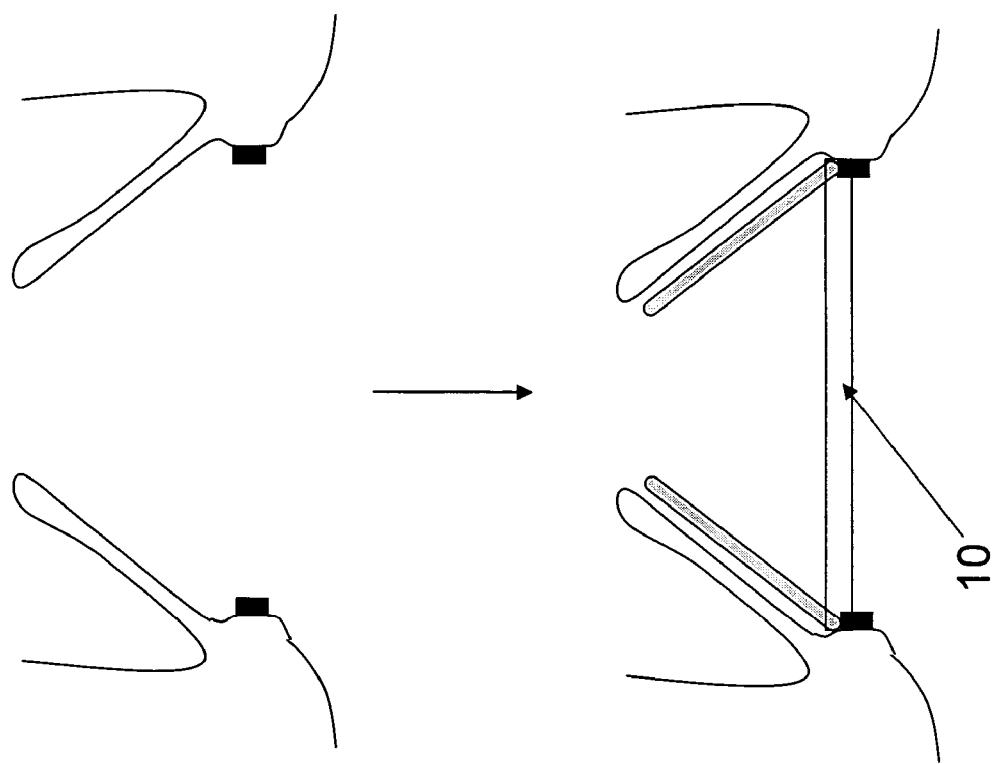

METHOD AND APPARATUS FOR ANCHORING IMPLANTS

CROSS-REFERENCES TO RELATED APPLICATIONS

This application claims priority to U.S. Provisional Patent Application Ser. No. 60/613,205, filed Sep. 27, 2004. The relevant disclosure of the application cited in this paragraph is hereby incorporated by reference.

BACKGROUND OF THE INVENTION

The present invention relates to the field of medical devices, in particular therapeutic vascular intervention devices requiring anchoring.

In the last few decades, therapeutic intervention in the cardiovascular arena has seen major advances in the reducing the invasiveness of life-saving procedures. In fact, coronary artery bypass has been surpassed, now, by coronary stenting in most patients with two or fewer lesions. Continuing this trend, several cardiovascular stents and valves have been designed to facilitate minimally invasive placement, frequently through the use of percutaneous catheter technologies.

While successful in several arenas, the minimally invasive placement of cardiovascular devices in areas of high flow or high stress has been relatively unsuccessful. This is due, in large part, to the migration of the devices after they have been placed but before they developed a firm attachment to the wall of the lumen. These issues are currently being seen in several percutaneous aortic valve technologies.

In an effort to combat the migration issue, several devices such as those found in Anduiza U.S. Pat. No. 6,875,231 and Anderson's U.S. Pat. Nos. 6,186,614, 5,840,081 and 5,411,552 are incorporating larger and larger support structures which span larger and larger sections of the lumen, causing issues related to side-branch obstruction and the requirement for anticoagulation. These devices also require a large degree of external pressure in the lumen in which they are anchored to be able to withstand the large migration-producing forces they face immediately post-implantation. Furthermore, these issues are also prevalent in percutaneous aortic aneurysm repair.

The current state of the art, then, would benefit from a minimally invasive method to firmly anchor cardiovascular and other types of devices in a low-profile, reversible manner using a minimum of hardware. The current invention provides this advance with a two-component procedure in which an anchoring element and an anchored device are placed in separate procedures. This two-part procedure allows for the anchoring element to be placed with enough lead time to allow for cellular ingrowth and firm anchoring prior to placement of the anchored device. Thus, before the device is attached, the physician will be able to visualize exactly where the device will be placed and the device will remain firmly in place once placed. After the anchoring element has been firmly embedded in the vascular wall, the anchored device (stent, valve, etc.) can be inserted and firmly attached to the anchoring element. The insertion of the device can also be accompanied by other interventions, ie native valve debridement. The present invention overcomes the limitations of the prior art by allowing for low-profile insertion into the lumen with a decreased risk of migration due to the presence of extensive tissue-ingrowth prior to exposing the anchored device to the migration-producing forces it will face immediately post-implantation.

SUMMARY OF THE INVENTION

As mentioned above, the current invention consists of two components, an anchoring element and the anchored device. When used in combination, the two components provide for the firm, minimally invasive anchoring of cardiovascular technologies. The anchoring element, itself, has three main functions: 1) to adhere to the vascular lumen, 2) to encourage fibrotic ingrowth, and 3) to provide a firm attachment site for the anchored device. The anchoring element has been designed to adhere to the lumen of the vessel using standard technologies including staples, clips, pins, stents, etc, made from standard materials, nitinol, stainless steel, etc., to provide for a firm attachment. The anchoring element, in the preferred embodiment, is coated with, or fabricated from, materials designed to encourage cellular ingrowth, such as loose weave dacron, polyester, etc, such that with adequate passage of time the element will become firmly embedded in the vessel wall. While this is the preferred embodiment, the present invention doesn't necessarily require this second feature as the benefit of reduction in invasiveness and precision in placement found with this two part procedure make the invention an advance in the field in and of themselves. The cellular ingrowth, though, is anticipated to be beneficial, though, and is considered preferable. The third component of the anchoring element provides for firm attachment of the anchored device. In its preferred embodiment this attachment mechanism is a reversible mechanical locking mechanism in the medial aspect of the anchoring element. This mechanism, though, could also consist of attraction by magnetism, chemical bonding, interference fit, etc.

The anchored device can consist of any implanted device requiring firm anchoring. The anchored device consists of the device body, whether it be a mitral valve, aortic valve, aortic aneurysm stent, gastrointestinal stent, etc., which firmly engages the anchoring element. In the case of a lengthy device, such as an aortic aneurysm stent or duodenal sleeve, multiple attachment rings may be placed on the device and multiple anchoring elements may be placed prior to deployment of the device. In this way both the proximal and distal aspects of the device can be firmly anchored once the device is deployed. Optionally, the proximal aspect of the device may be the only portion of the device which attaches to the anchoring element and the distal portion of the device, which requires less mechanical strength, may simply use standard anchoring mechanisms, such as staples, clips, pins, stents.

In its preferred embodiment, then, the anchoring element is placed at the desired site and is then given at least a week to allow for cellular ingrowth, after which the patient then has the device placed. The device then, is held firmly in place using natural cellular and fibrotic reactions thus reducing the requirement for complex and extensive anchoring hardware. The device placement and anchoring element placement, while separate procedures, may be less invasive than any single procedure due to the drastic reduction in required hardware for each procedure. The anchored device addresses a number of the critical issues limiting deployment of existing technologies. Specifically, the anchored device will facilitate precise, secure positioning of the implant without the need for excessive pressures on the wall of the lumen or overly aggressive, but ineffective, anchoring mechanisms at the time of placement of the anchored device. One such example includes the use of an anchoring element placed in the vicinity of the pyloric sphincter, either on the sphincter itself or adjacent to the sphincter in the duodenum or the stomach, then allowing time for tissue ingrowth prior to placement of the complementary anchored device, ie gastric or duodenal electrical stimulator, duodenal sleeve, pyloric sphincter restrictor, etc. This mechanism will allow for the placement of gastrointestinal, as well as other, technologies using much less hardware and with a decreased risk of perforation or migration of the anchored device.

The device will provide the following advances over the current state of the art: (1) Facilitation of self-seating and avoidance of coronary ostia or other sensitive regions; (2) Elimination of the frequent complication of migration and inadequate sizing with the anchoring of a device with a known diameter to native tissue; (3) Incorporation of radiographic contrast into part one of the anchored device will facilitate localization of the coronary ostia prior to placing the valve and also facilitate exact positioning/orientation of the implant. This feature will also facilitate visualization of real-time fluoroscopic landmarks during placement of the implant; (4) Encouragement of native tissue ingrowth into the anchoring element with the embedding of elements in the anchor material that would encourage cellular ingrowth (especially important in the setting of a potentially calcified aorta). This last feature will allow for a greatly decreased footprint of the overall device and use of much less hardware in anchoring the device.

While the preferred embodiment has been described as an anchoring element to anchor devices within a lumen, the anchoring element may also consist of a ring, a tube, a socket, a port, a catheter, a patch or any other fastener allowing for firm engagement of the complementary region of the anchored device. The mechanism for firm engagement may be an interference fit, locking, screw-type or magnetically coupled device, but is not limited to these options as an firm engagement mechanism will suffice.

Also, while the anchored device, in the preferred embodiment, has been described as a cardiovascular device, the anchored device may consist of one or more of several devices including, but not limited to: prosthetic aortic, tricuspid or mitral heart valves, abdominal aortic aneurysm stents, coronary stents, gastrointestinal stents, gastrointestinal devices anchored in the esophagus, stomach or duodenum, gastrointestinal devices anchored within the gastrointestinal lumen, urologic devices anchored within the bladder, peritoneal devices anchored within the peritoneum, pulmonary devices anchored within the pulmonary tree, nasopharyngeal devices anchored within the nasopharynx, orthopedic devices anchored into bone and/or dermatologic devices anchored into the skin or subcutaneous tissues.

The competitive advantages of the present invention include: Firm anchoring of device with reduced migration risk, exact placement of device, and reduced invasiveness due to reduction in hardware requirements and overall footprint of the implanted device.

BRIEF DESCRIPTION OF THE DRAWINGS

FIG. 2—Longitudinal section of the anchoring element deployed in the supravalvular position with clips, staples, etc FIG. 3—Longitudinal section of the anchoring element deployed in the subvalvular position with clips, staples, etc FIG. 4—Aerial cross-section view of the anchoring element's entire circumference with clips FIG. 5A-B—Possible deployment mechanism for anchoring element FIG. 6A-B—Longitudinal section of the anchoring element deployed in the subvalvular position (FIG. 6A) with clips illustrating fibrotic ingrowth (FIG. 6B).

FIG. 7A-B—Longitudinal section of the anchoring element deployed in the subvalvular position illustrating fibrotic ingrowth (FIG. 7A) and subsequent device deployment and attachment to the anchoring element with debridement of the native valve (FIG. 7B)

FIG. 8A-B—Longitudinal section of the anchoring element deployed in the subvalvular position illustrating fibrotic ingrowth (FIG. 8A) and subsequent device deployment and attachment to the anchoring element without debridement of the native valve (FIG. 8B)

DETAILED DESCRIPTION OF THE PREFERRED EMBODIMENTS

Figure 1:
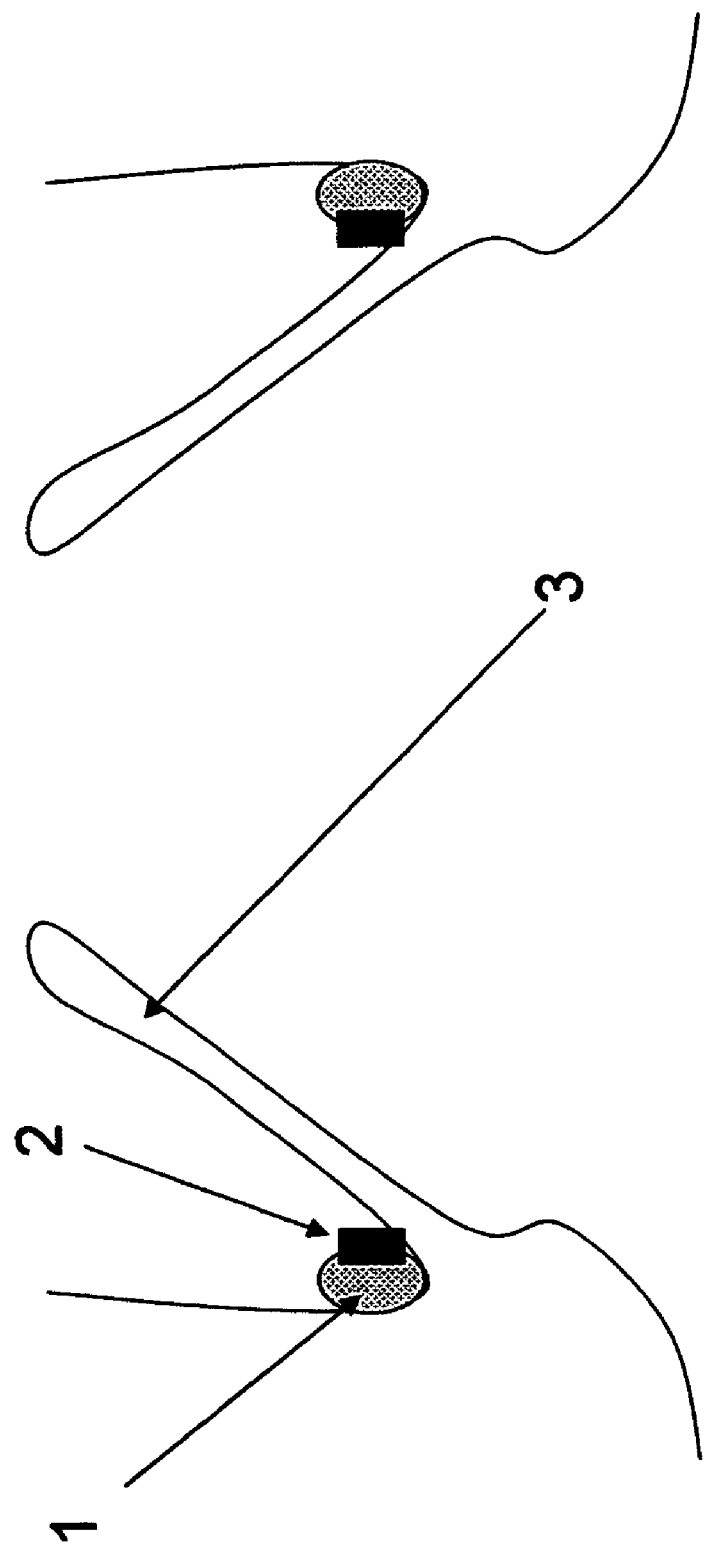
FIG. 1—Longitudinal section of the anchoring element deployed in the supravalvular position with interference fit and without clips, staples, etc.

FIG. 1—This illustration represents the deployed anchoring element placed in the aortic valve region. As can be seen from the illustration, the anchoring element consists solely of a material to promote fibrotic ingrowth 1 and the attachment ring 2 designed to engage the aortic valve device. In this case, the device is deployed above the native aortic valve 3.

FIG. 2—This illustration represents the deployed anchoring element again placed in the aortic valve region but this time with clips to secure the anchoring element to the aorta. As can be seen from the illustration, the anchoring element consists of a material to promote fibrotic ingrowth 1, the attachment ring 2 designed to engage the aortic valve device and clips, staples, etc 4 for the attachment of the anchoring element to the aortic tissues. In this case, the device is deployed above the native aortic valve.

FIG. 3—This illustration represents the deployed anchoring element again placed in the aortic valve region but this time with clips to secure the anchoring element. As can be seen from the illustration, the anchoring element consists of a material to promote fibrotic ingrowth 1, the attachment ring 2 designed to engage the aortic valve device and clips, staples, etc 4 for the attachment of the anchoring element to the aortic tissues. In this case, the device is deployed below the native aortic valve.

Figure 4:
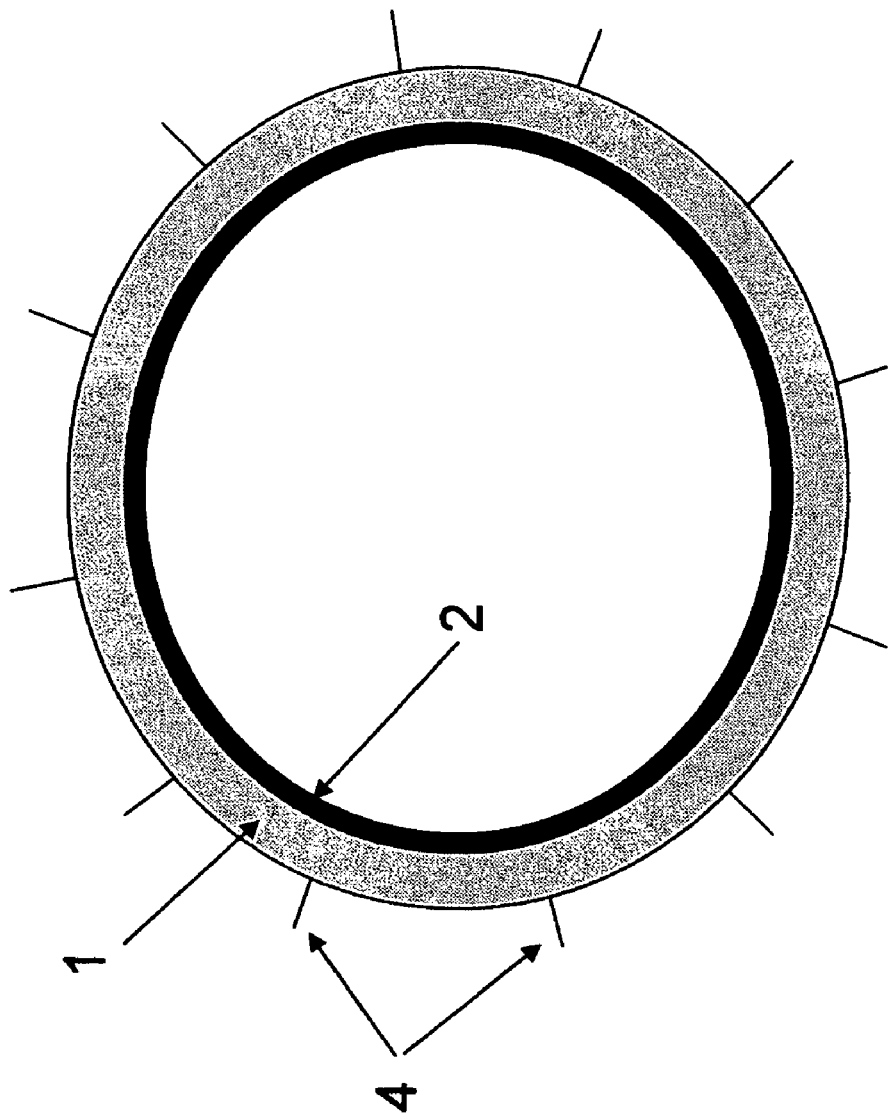

FIG. 4—Is an aerial cross-section view of the anchoring element's entire circumference with clips. In this view the entire circumference of the fibrotic ingrowth anchoring element 1 and the device attachment ring 2 can be visualized as can the clips 4 to secure the device to native tissues. In this case the anchoring element is attached with clips, but it could be attached with a expanding stent, staples, sutures, glues or other attachment modalities.

Figures 5A, 5B:
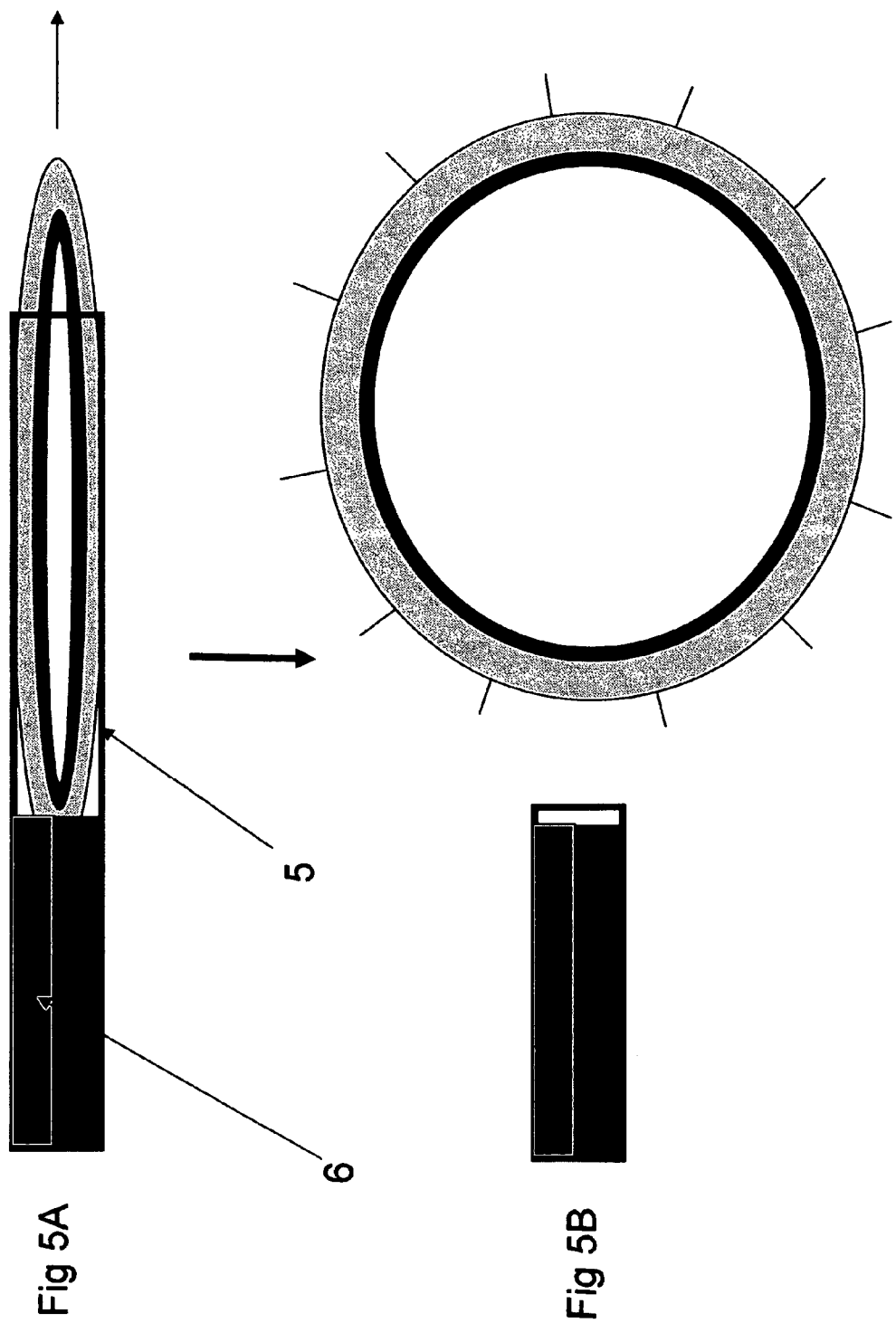

FIG. 5—Is a view of a possible deployment mechanism for the anchoring element. In this case the anchoring element is placed inside of an insertion tube or catheter 5 and placed in the region where deployment is desired. A plunger 6 is then used to expel the device into its proper position. This is but one of many possible deployment mechanisms with the optimal embodiment being a deployment mechanism that allows for reversible circumferential deployment in a consistent manner.

FIG. 6A-B—Longitudinal section of the anchoring element deployed in the subvalvular position (FIG. 6A) with clips illustrating fibrotic ingrowth (FIG. 6B). In this case, the subvalvular clips hold the anchoring element in place until the cellular and fibrotic ingrowth can provide for firm permanent attachment 7.

FIG. 7A-B—In this longitudinal section of the anchoring element deployed in the subvalvular position fibrotic ingrowth (FIG. 7A) and subsequent device deployment to the anchoring element with debridement of the native valve (FIG. 7B) are illustrated. Once the anchoring element has been firmly anchored by fibrotic ingrowth, the new aortic valve 9 may be placed with or without removal of the existing native valve 8.

FIG. 8A-B—Longitudinal section of the anchoring element deployed in the subvalvular position illustrating fibrotic ingrowth (FIG. 8A) and subsequent device deployment to anchoring element without debridement of the native valve (FIG. 8B). Here the aortic valve device 10 is placed without removal of the native valve.

Figure 9:
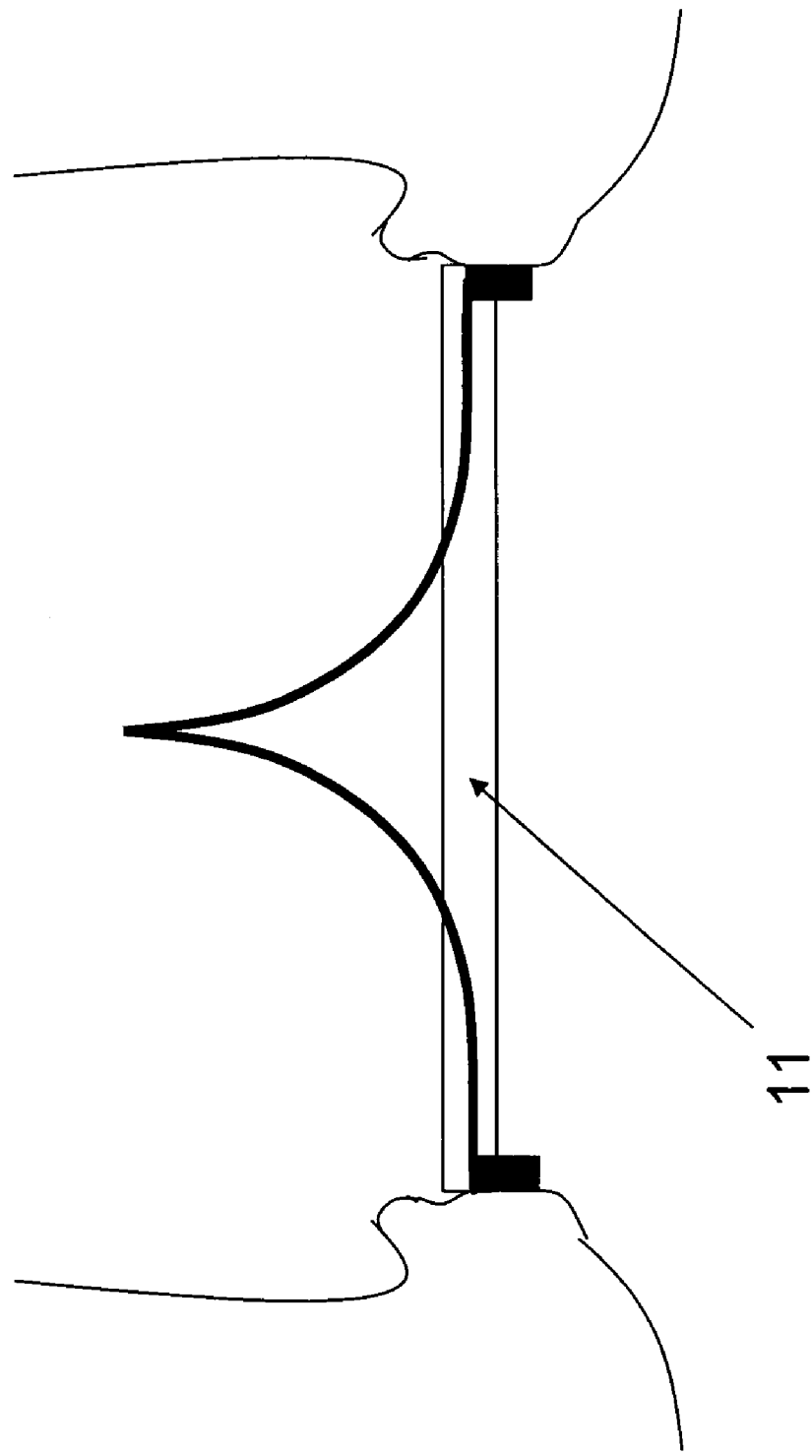
FIG. 9—Longitudinal section of the anchoring element deployed in the subvalvular position illustrating fibrotic ingrowth and subsequent deployment of porcine valve to the anchoring element with debridement of the native valve.

FIG. 9—Longitudinal section of the anchoring element deployed in the subvalvular position illustrating fibrotic ingrowth and subsequent deployment of porcine valve 11 to anchoring element with debridement of the native valve.

Figure 10:
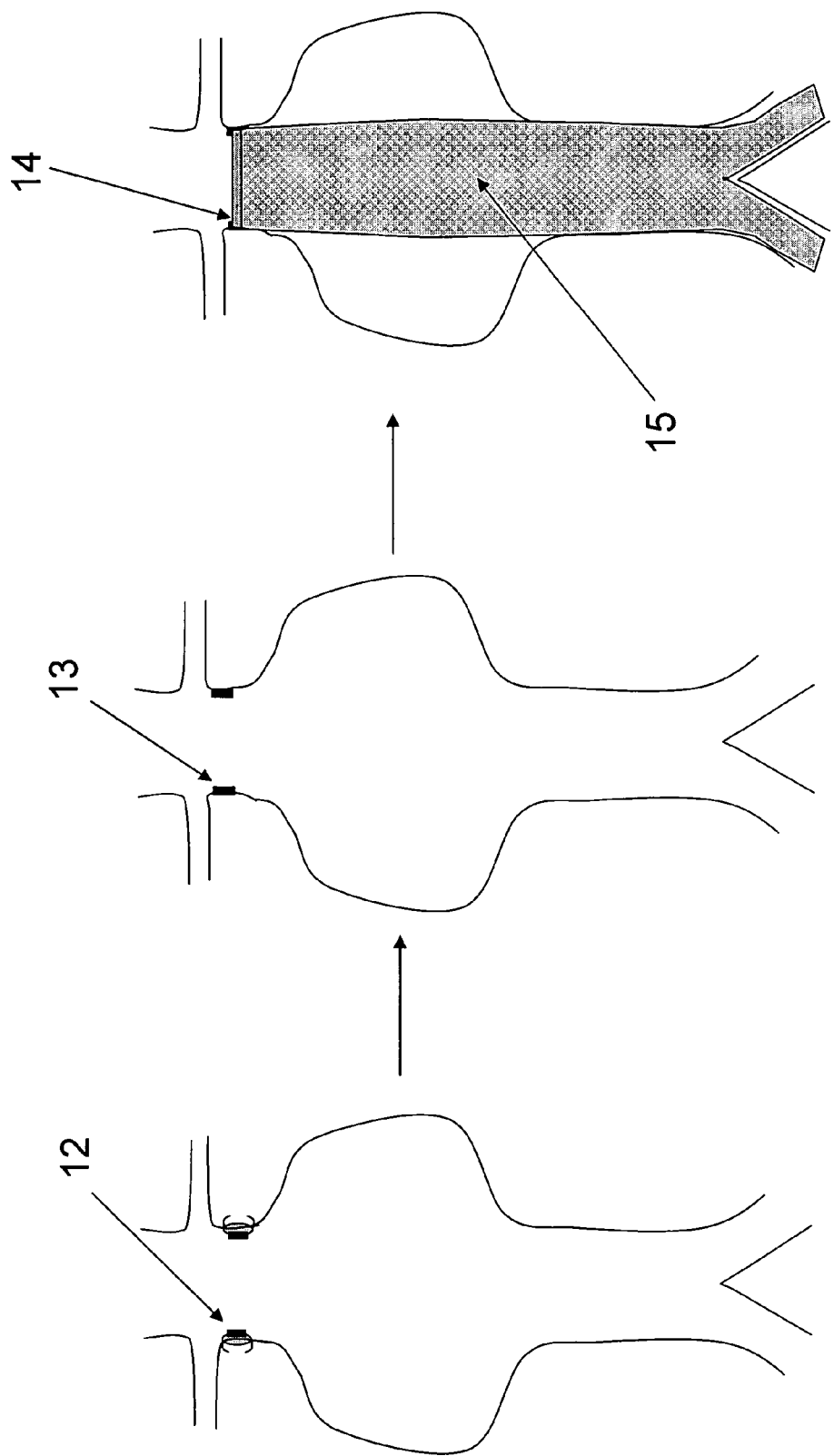
FIG. 10A-C—Longitudinal section of the anchoring element deployed with clips in the abdominal aorta (FIG. 10A) illustrating fibrotic ingrowth (FIG. 10B) and subsequent deployment of abdominal aortic aneurysm stent to anchoring element (FIG. 10C)

FIG. 10A-C—Longitudinal section of the anchoring element deployed with clips in the abdominal aorta 12 (FIG. 10A) illustrating fibrotic ingrowth 13 (FIG. 10B) and subsequent deployment of abdominal aortic aneurysm stent 15 to the anchoring element 14 (FIG. 10C). In this case the anchoring element has been deployed just below the renal arteries and just above the neck of the aneurysm. As can be seen in this case, this invention allows for much more precise placement of abdominal aortic stents in much tighter regions than would otherwise be possible with existing longer stent-based devices.

Figure 11:
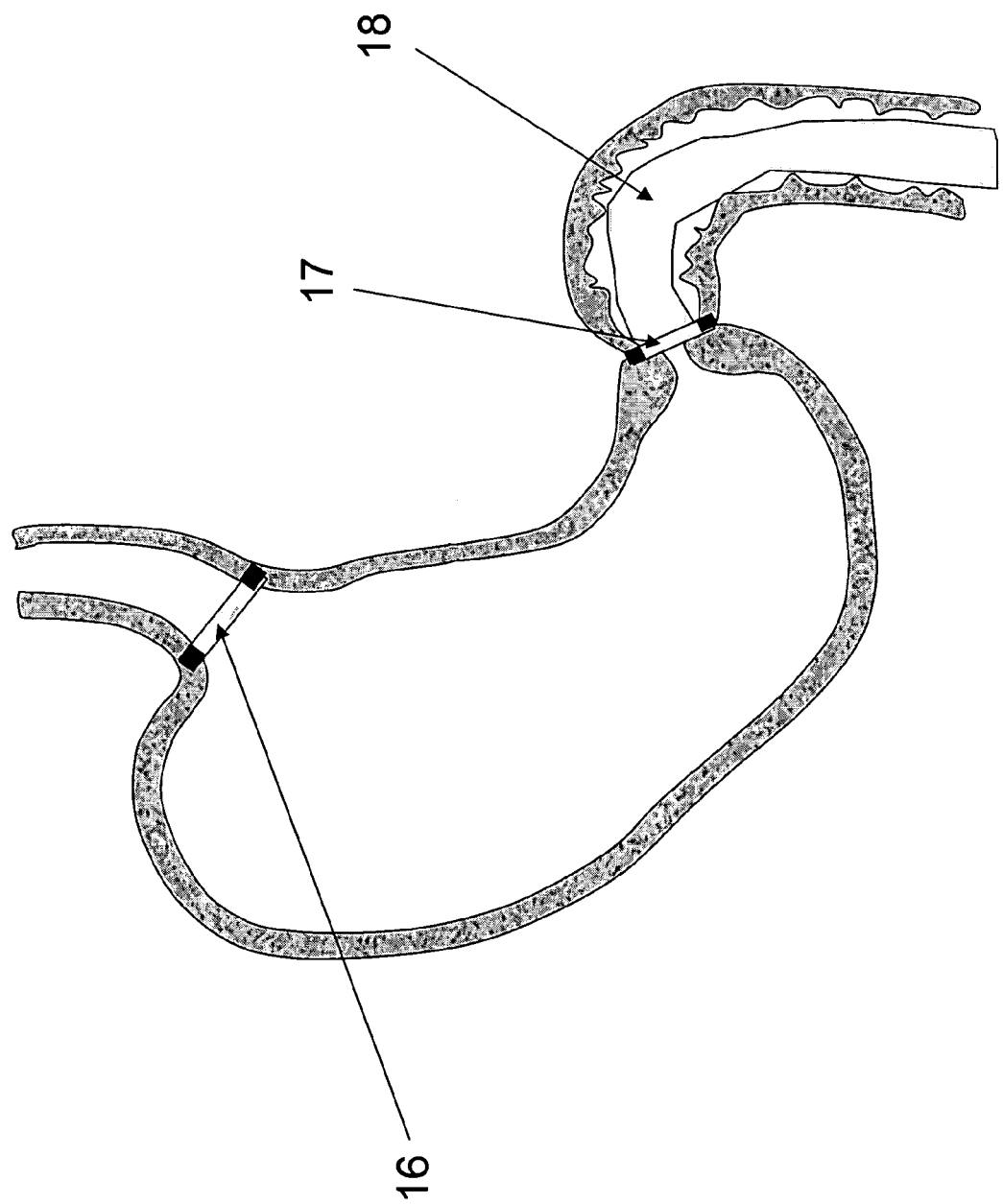
FIG. 11—Cross-section of the gastrointestinal tract anchoring embodiment illustrating anchoring of a lower esophageal ring and a pyloric ring to which a intestinal sleeve is attached FIG. 12—Cross-section of the gastrointestinal tract anchoring embodiment wherein an electrical stimulator for the treatment of obesity is shown attached to a pyloric anchoring element

FIG. 11—Cross-section of the gastrointestinal tract anchoring embodiment illustrating anchoring of a lower esophageal ring 16 and a pyloric ring 17 to which a intestinal sleeve is attached 18. These are but two of the possible embodiments of the gastrointestinal devices that can be anchored using this technology with other possibilities including, but not limited to: an intestinal sleeve, an electrical stimulator designed to alter transit or treat obesity, for an artificial rectum, a gastric pouch for the treatment of obesity and a flow restrictor for gastrointestinal transit.

Figure 12:
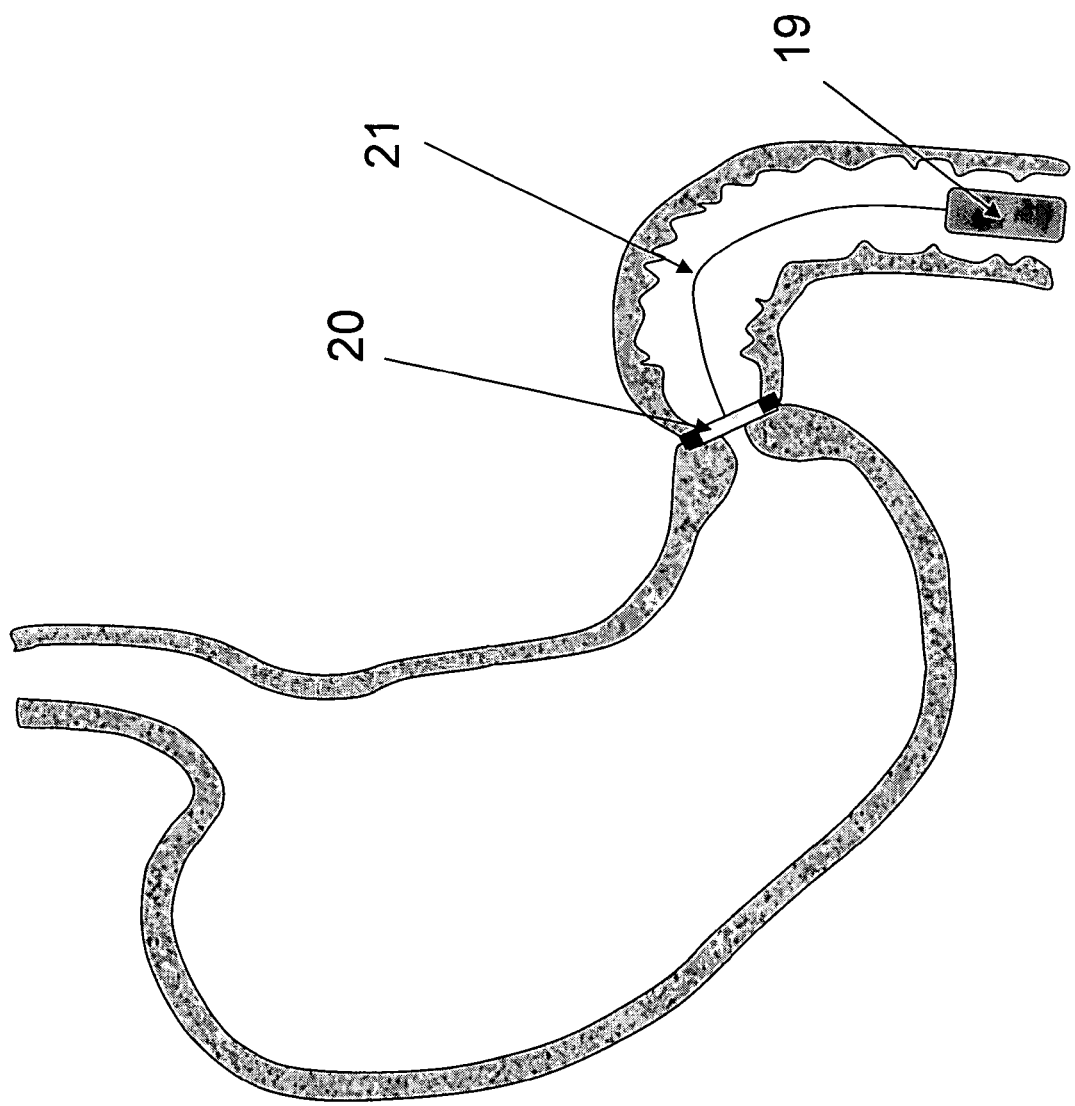

FIG. 12—Cross-section of the gastrointestinal tract anchoring embodiment wherein an electrical stimulator for the treatment of obesity 19 is shown anchored to the pyloric anchoring element 20, in this case via an optional conducting tether 21. The anchoring element may be in the pyloric, cardiac or fundic regions of the stomach or may be attached to the esophagus or intestine. The tether may not be used in the instance where the stimulator is low-enough profile that it will not overly impede flow through the gastrointestinal tract and cause a bowel obstruction. The anchoring element may consist of the ring illustrated, but may also consist of any configuration of ingrowth encouraging material (including stapling, suturing, etc, at a single, non-circumferential site) deployed in any region of the stomach, esophagus or intestine. In the preferred embodiment, the anchoring element is deployed in a non-mucosal region of the stomach, esophagus and/or intestine in order to avoid erosion, ulceration and/or rupture.

We claim:

1. A multi-component anchoring device comprising:
   an anchoring element anchorable to a bodily surface, the anchoring element comprising,
      a fibrotic ingrowth portion having a material which promotes fibrotic ingrowth and is configured for anchoring the anchoring element to the bodily surface by fibrotic ingrowth, and
      an attachment portion coupled to the fibrotic ingrowth portion and having a reversible locking mechanism positioned along a medial aspect of the anchoring element; and
   an anchored device separated from the anchoring element and which is couplable to the attachment portion in vivo while the anchoring element remains anchored to the bodily surface by the fibrotic ingrowth, wherein the anchored device is self-seating along the attachment portion when secured to one another.

2. The multi-component anchoring device of claim 1, wherein the anchoring element comprises one or more support elements providing for a firm attachment of the anchoring element to the bodily surface at the time of implantation of the anchoring element on the bodily surface.

3. The multi-component anchoring device of claim 2, wherein the one or more support elements are staples, clips, pins, stents, or sutures.

4. The multi-component anchoring device of claim 1, wherein the fibrotic ingrowth portion comprises a coating that promotes cellular ingrowth.

5. The multi-component anchoring device of claim 1, wherein the fibrotic ingrowth portion comprises a fabric material.

6. The multi-component anchoring device of claim 1, wherein the attachment portion comprises a ring, a tube, a socket, a port, a catheter, a patch, or a fastener.

7. The multi-component anchoring device of claim 1, wherein the attachment portion comprises a reversible mechanical locking mechanism.

8. The multi-component anchoring device of claim 1, wherein the attachment portion is configured for coupling the anchored element by screwing, magnetic coupling, chemical bonding, or interference fit.

9. The multi-component anchoring device of claim 1, wherein the anchored device comprises a contrast element facilitating localization of an anatomic landmark and an exact positioning of the anchored device.

10. The multi-component anchoring device of claim 1, wherein the anchored device is one or more of a prosthetic aortic, tricuspid or mitral heart valve, an abdominal aortic aneurysm stent, a coronary stent, a gastrointestinal stent, a gastrointestinal device anchored in the esophagus, stomach or duodenum, a gastrointestinal device anchored within the gastrointestinal lumen, a urogynecologic device anchored within the bladder, uterus, fallopian tubes or vagina, a peritoneal device anchored within the peritoneum, a pulmonary device anchored within the pulmonary tree, a nasopharyngeal device anchored within the nasopharynx, an orthopedic device anchored into bone, or a dermatologic device anchored into skin.

11. The multi-component anchoring device of claim 1, wherein the anchoring element is foldable to fit within a delivery catheter.

12. A method of anchoring an implanted device comprising:

anchoring an anchoring element to a bodily surface, the anchoring element comprising a fibrotic ingrowth portion configured for coupling the anchoring element to the bodily surface by fibrotic ingrowth and an attachment portion coupled to the fibrotic ingrowth portion;

allowing fibrotic ingrowth to occur on the fibrotic ingrowth portion along the bodily surface over a period of at least a week; and coupling the implanted device to the attachment portion after the anchoring element has been anchored to the bodily surface for at least the week.

13. The method of claim 12, wherein providing the anchoring element comprises providing one or more support elements providing for a firm attachment of the anchoring element to the bodily surface at the time of implantation of the anchoring element on the bodily surface.

14. The method of claim 13, wherein providing the one or more support elements comprises providing staples, clips, pins, stents, or sutures.

15. The method of claim 12, wherein providing the fibrotic ingrowth portion comprises providing a coating that promotes cellular ingrowth.

16. The method of claim 12, wherein providing the fibrotic ingrowth portion comprises providing a fabric material configured for fibrotic ingrowth.

17. The method of claim 12, wherein providing the attachment portion comprises providing a ring, a tube, a socket, a port, a catheter, a patch, or a fastener.

18. The method of claim 12, wherein providing the attachment portion comprises providing a reversible mechanical locking mechanism.

19. The method of claim 12, wherein the anchored device is coupled to the attachment portion by screwing, magnetic coupling, chemical bonding, or interference fit.

20. The method of claim 12, wherein coupling to the anchored device comprises providing the anchored device with a contrast element facilitating localization of an anatomic landmark and an exact positioning of the anchored device.

21. The method of claim 12, wherein coupling the anchored device comprises coupling one or more of a prosthetic aortic, tricuspid or mitral heart valve, an abdominal aortic aneurysm stent, a coronary stent, a gastrointestinal stent, a gastrointestinal device anchored in the esophagus, stomach or duodenum, a gastrointestinal device anchored within the gastrointestinal lumen, a urogynecologic device anchored within the bladder, uterus, fallopian tubes or vagina, a peritoneal device anchored within the peritoneum, a pulmonary device anchored within the pulmonary tree, a nasopharyngeal device anchored within the nasopharynx, an orthopedic device anchored into bone, or a dermatologic device anchored into skin.

22. The method of claim 12, further comprising the steps of:

folding the anchoring element within a delivery catheter; and delivering the anchoring element to the bodily surface by ejecting the anchoring element from the delivery catheter.

* * * * *